United States Patent [19]

Howard et al.

[11] Patent Number: 4,678,488

[45] Date of Patent: Jul. 7, 1987

[54] LIQUID SEPARATOR FOR GAS ANALYZER

[75] Inventors: Charles P. Howard, Ann Arbor, Mich.; Donald H. Stedman, Englewood, Colo.

[73] Assignee: Sensors, Inc., Saline, Mich.

[21] Appl. No.: 729,635

[22] Filed: May 2, 1985

[51] Int. Cl.$^4$ ............................................. B01D 45/14
[52] U.S. Cl. ........................................ 55/406; 55/429; 55/431; 55/DIG. 17; 73/863.21; 73/863.45; 73/863.56; 422/101
[58] Field of Search ................. 55/203, 400, 406, 429, 55/431, 469, DIG. 17; 422/101; 73/863.21, 863.45, 863.56; 494/900

[56] References Cited

U.S. PATENT DOCUMENTS

| | | | |
|---|---|---|---|
| 2,392,124 | 1/1946 | Denys | 55/406 |
| 3,498,454 | 3/1970 | Timson | 55/400 |
| 3,853,516 | 12/1974 | Lyshkow | 55/429 |
| 4,197,858 | 4/1980 | Osborn | 128/718 |
| 4,304,578 | 12/1981 | Hakala et al. | 55/189 |
| 4,324,557 | 4/1982 | Wegstedt | 55/203 |
| 4,514,198 | 4/1985 | Develle et al. | 55/431 |

FOREIGN PATENT DOCUMENTS 448140 6/1936 United Kingdom ................ 55/406

OTHER PUBLICATIONS

Anesthesiology News, vol. 7, No. 2, Feb. 1981, pp. 1, 26, 27, Gould Capnographs State-of-the-Art Carbon Dioxide Analyzers, Gould Electronics & Electrical Products.
Critikon, GM1/383R, Respiratory Gas Monitor Detects Gas Changes as They Occur.
Jeffrey B. Riker, Barry Haberman, Expired Gas Monitoring by Mass Spectrometry in a Respiratory Intensive Care Unit, Critical Care Medicine, vol. 4, No. 5, 1976, pp. 223-229.
Pyles, Stephen T. et al, Expiratory Valve Dysfunction in a Semiclosed Circle Anesthesia Circuit, Verification by Analysis of Carbon Dioxide Waveform, Anesth. Analg., 1984, pp. 536-537.
Expected Accuracy of Various Machine Processes, Metal Processing, Table 10-9, p. 859.
Abandoned patent application Ser. No. 367,762 filed 4/12/82 to Howard.

*Primary Examiner*—David L. Lacey
*Attorney, Agent, or Firm*—Price, Heneveld, Cooper, DeWitt & Litton

[57] ABSTRACT

A liquid separator for a gas analyzer is provided comprising a sample gas inlet; a sample gas outlet; and a separation chamber in fluid communication with the gas inlet and gas outlet. The separation chamber is provided with a smooth, planar upper wall and a smooth planar lower wall, the upper and lower walls being substantially parallel and having a small uniform clearance therebetween. A motor is provided for rotating the lower wall of the separation chamber about a central axis normal to the surfaces of the upper and lower walls. The gas outlet is disposed on the central axis of the rotating lower wall. The gas inlet is disposed off of the central axis. A vacuum is applied to the sample gas outlet to draw sample gas through the separation chamber. A collection chamber is provided which surrounds the separation chamber for receiving liquids and other debris separated from the sample gas flow by contact with the rotating lower wall and centrifugal acceleration imparted thereto by the lower wall. A vacuum is also applied to the collection chamber to facilitate the exhaust of liquid and other debris from the separation chamber. The rapid response time and low flow rates of the separator make it particularly suitable for use in breath-by-breath, human gas analysis such as the art of capnography.

15 Claims, 2 Drawing Figures

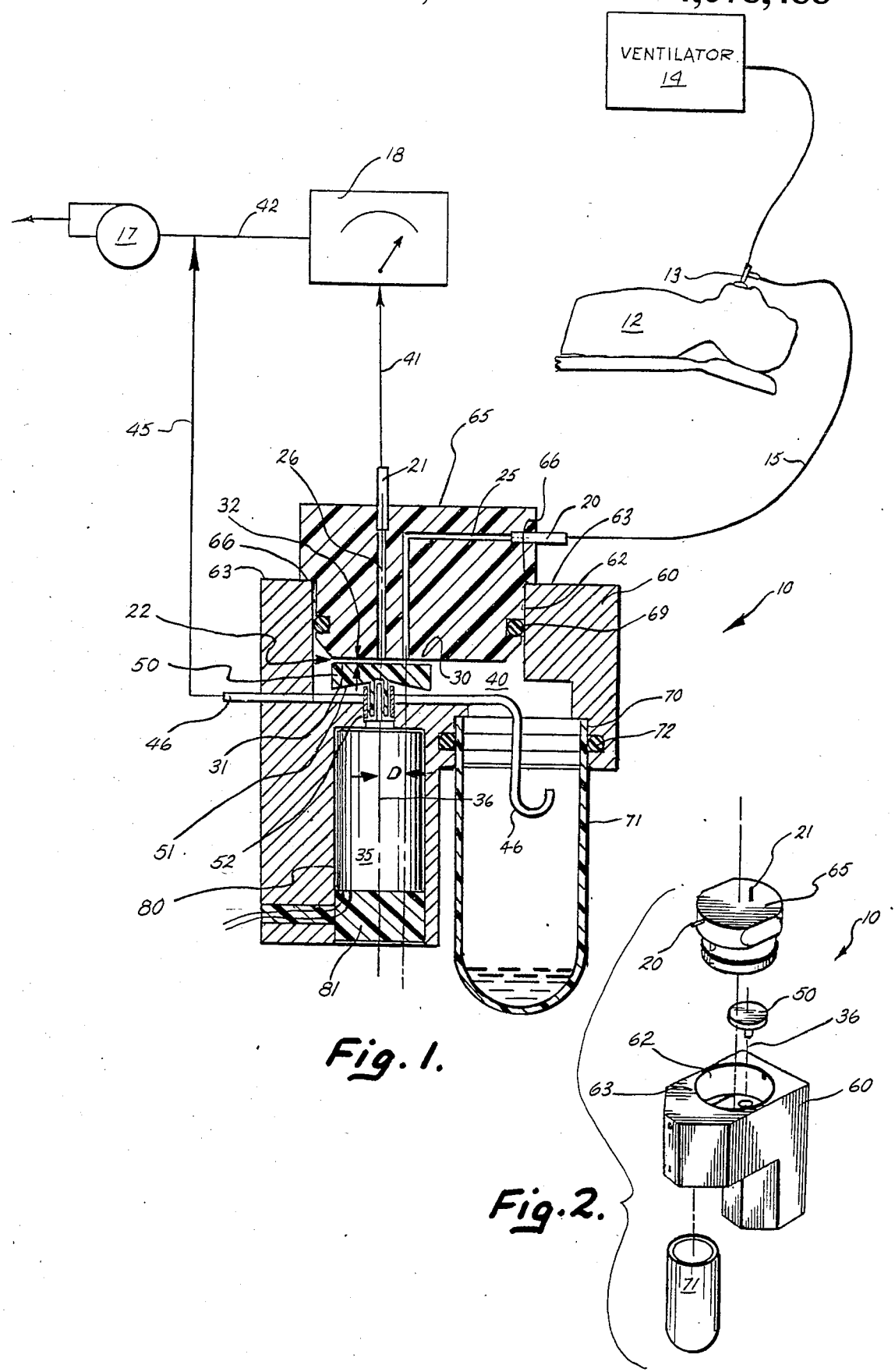

LIQUID SEPARATOR FOR GAS ANALYZER

BACKGROUND OF THE INVENTION

The invention relates generally to water traps or liquid sepators, and more particularly, is directed to a liquid separator that solves unique problems associated with removing water, liquids and other debris from the sample gas in a gas analyzer.

Both dispersive and nondispersive radiant energy gas analyzers are used in the prior art to measure certain predetermined constituents of a sample gas containing contaminants such as water, which interfere with the operation of the analyzer. For example, nondispersive type infrared gas analyzers are currently used for breathing gas analysis, both in the medical field and the law enforcement field. In the medical field, such analyzers are used to determine the concentration of a wide variety of gases in a patient's breath. For example, the art of capnography involves the precise measurement of carbon dioxide concentrations in the breathing gas of a patient. This data, if accurate, is quite useful in determining a patient's ventilatory status as well as other physiological conditions. In the law enforcement field, nondispersive analyzers have been used for determining ethanol concentration in the breathing gas expelled from a driver's lungs. In both of these applications, water, liquids and other debris are often expelled from the subject along with breathing gases.

In the past, attempts to remove liquids from the sample gas flow in such analyzers have generally involved the use of a simple water trap comprising a cannister or housing substantially filled with a water absorbing material. The housing is provided with an inlet and an outlet for passing sample gas through the housing and the absorber material contained therein. The problem with this type of water trap stems from the detrimental effect that it has on the response time of the analyzer and its limited capacity. In the art of breath-by-breath analysis, the available volume of sample gas can be quite small and this type of water trap impairs the response time of the analyzer because of its relatively large volume and the mixing of sample gas in the trap. When the size of the water trap housing is reduced to a point at which the volume of the housing is low enough to have a negligible effect on the response time of the analyzer, the amount of absorbent retained within the housing no longer provides a satisfactory water absorbing capacity.

This problem is found to be particularly acute in the field of capnography, where it is important to obtain a continuous and very accurate measure of the carbon dioxide content in the end tidal portion of a patient's breathing gases. Such analyzers are often referred to as capnographs. While the volume of a normal adult patient's lungs is substantial, only a portion of the breath is analyzed, namely, the last portion of the breath expelled or end tidal portion. This problem is, of course, exacerbated in children and neonatals.

High levels of secretions are encountered in patients that are anesthetized or patients that are in critical care situations. These patients are normally supplied highly humidified gases. The condition of the patient is often such that mucous, sputum and/or blood can be present in the sample tube as well as condensed water. The sample tubes are small because the sample is small and thus blockages from such high viscosity liquids are common. Heating of the sample tube to prevent condensate from interfering with the operation of the analyzer further promotes the build-up of these highly viscous liquids. Such blockages interfere with gas flow and flow profile. This is intolerable in a capnograph which must be reliable, accurate and highly responsive.

The misnomer "water trap" is often applied to liquid collection devices that are used to strip contaminants from the sample flow in a capnograph. If water was the only fluid to contend with then other solutions are possible. In the past, large area collection vials (discussed above) or tortuous path water traps have been used to deposit or accelerate liquid particles out of the sample gas flow, respectively. The large area fluid traps are effective in separating liquids from sample gas but so greatly reduce the response time of the capnograph that physiological data cannot be truly recorded (i.e. transient changes in respiratory gas are completely damped). The tortuous path traps function relatively well on entrained pure water, but high viscosity fluids are not easily accelerated out of the gas path.

While most analyzers used in capnography to determine carbon dioxide concentration are relatively simple and cost effective, the efficacy of these instruments has sparked a continuous debate among physicians because of slow response and frequent failures. Monitoring of patients in the operating room or critical care situations is desirable, but physicians have, through experience, developed reservations concerning their use because of the failure reputation of these instruments.

SUMMARY OF THE INVENTION

According to the present invention, these and other problems in the prior art are solved by the provision of a liquid separator for a gas analyzer comprising a sample gas inlet; a sample gas outlet; and a separation chamber in fluid communication with the gas inlet and gas outlet. The separation chamber is provided with a smooth, planar, upper wall and a smooth, planar, lower wall. The upper and lower walls are substantially parallel and have a small, uniform clearance therebetween. The lower wall is disposed on a generally planar disk which is mounted on the output shaft of a high speed electric motor. The output shaft of the electric motor and the disk are rotated about a central axis which is normal to the surfaces of both the upper and lower walls of the separation chamber. The gas outlet is disposed on the central axis of the separation chamber. The gas inlet is disposed a predetermined distance off the central axis. A collection chamber is provided which surrounds the separation chamber. A vacuum pump is connected to the gas outlet for drawing sample gas through the separation chamber. As the sample gas is drawn through the gas inlet into the separation chamber it impinges the lower surface of the separation chamber and is immediately accelerated to the speed of the disk. The heavier mass components are centrifugally accelerated outwardly into the surrounding collection chamber and the sample gas spirals inwardly where it is drawn into the centrally located sample gas outlet. The vacuum pump is also connected to the collection chamber through a flow restrictor to supply an equal or similar vacuum to the collection chamber thus equalizing the pressure drop across the disk and facilitating the exhaust of liquid and other debris from the separation chamber

BRIEF DESCRIPTION OF THE DRAWINGS

FIG. 1 is an elevational view, in section, of the liquid separator of the present invention.

FIG. 2 is an exploded assembly of the liquid separator of the present invention.

DESCRIPTION OF THE PREFERRED EMBODIMENTS

With reference to the figures, the liquid separator of the present invention is generally illustrated at 10. The liquid separator illustrated at 10 is particularly suitable for use in removing liquids and other debris from the sample gas flow in a breath-by-breath carbon dioxide gas analyzer used in the art of capnography. As described above, the art of capnography involves the breath-by-breath analysis of the carbon dioxide content of the end tidal gases of an anesthetized patient or a patient in critical care. As schematically illustrated in FIG. 1, the patient 12 may be fitted with an intubation tube 13 and may be connected to a ventilator 14. Most importantly, however, for breath-by-breath analysis, the output of the patient's lungs is sampled by line 15 which receives a portion of the gas expelled by the patient through the intubation tube 13. Sample gas is drawn sequentially through the line 15 to the liquid separator 10 and a gas analyzer 18 by a vacuum pump 17. The gas analyzer 18 is normally a nondispersive, infrared, carbon dioxide gas analyzer. The design of such gas analyzers and their application to the art of capnography is well-known. In capnography, the portion of the patient's breathing gases which must be analyzed is the end tidal portion or that very last portion of the breathing gases expelled from the patient's lungs. This sample is very small and often contains water vapor, condensate, sputum, mucous and/or blood. These materials completely mask the output of a nondispersive gas analyzer if they reach the sample chamber within the analyzer. Thus, it is imperative to provide a highly efficient liquid separator for removing these liquids and any other debris which is entrained in the sample gas flow. However, because very small flow rates are involved, the response time of the liquid separator is critical, and in fact, it should take less than 100-150 milliseconds to pass a representative sample of the sample gas through the liquid separator 10. While these requirements are particularly acute in the art of capnography, it should be understood that the liquid separator of the present invention is equally applicable to other types of gas analyzers used in breath-by-breath analysis or in some other type of analysis involving a very small contaminated sample gas flow.

The liquid separator of the present invention comprises a sample gas inlet 20 and a sample gas outlet 21. A separation chamber is disposed at 22, the separation chamber 22 being in fluid communication with the gas inlet 20 and the gas outlet 21 through inlet and outlet manifolds 25 and 26, respectively. The separation chamber comprises a very smooth, planar, upper wall 30 and a very smooth, planar, lower wall 31. The upper and lower walls 30 and 31 are substantially parallel and have a small uniform clearance 32 disposed therebetween. Although, in this embodiment the walls 30 and 31 are disposed one atop the other in a horizontal orientation, and the walls are consistently identified as upper and lower walls, the orientation of the walls is not critical to the operation of the separator. In other embodiments of the invention the walls may even be given a vertical orientation.

A high speed electric motor is provided at 35 for rotating the lower wall 31 about a central axis 36 which is normal to the surfaces of the upper and lower walls 30 and 31. The outlet manifold 26 receives the sample gas from the separation chamber 22 at a point disposed on the central axis 36. The inlet manifold 25 delivers sample gas to the separation chamber 22 at a point displaced a predetermined distance D from the central axis 36. A collection chamber 40 is provided which surrounds the separation chamber 22. The collection chamber 40 receives liquids and other debris which are separated from the sample flow by contact with the rotating lower wall 31 and centrifugal acceleration imparted thereto by the rotating wall. The vacuum pump 17 applies a negative pressure to the outlet manifold 26 through lines 41 and 42 to draw sample gas sequentially through the separation chamber 22 and gas analyzer 18. The vacuum pump 17 is also connected to the collection chamber 40, through a series flow restrictor not illustrated herein, by line 45 connected to sump exhaust 46. This application of a similar or equal vacuum to the collection chamber 40 equalizes the pressure drop across the separation chamber 22 and facilitates the expulsion of liquid and other debris from the separation chamber.

The lower wall 31 is preferably disposed on the top of a generally disk-shaped member 50 which is mounted for rotation on the output shaft of high speed motor 35. As previously explained, the output shaft of the motor 35 is coincident with the central axis 36 of the separation chamber 22 and preferably, the disk 50 is provided with a central bore which is mounted on the output shaft of the motor 35 with a simple interference fit. This renders the disk-shaped member 50 manually demountable to facilitate replacement and/or cleaning of the disk. The lower surface 51 of the disk-shaped member 50 is provided with a concave, generally conical surface which, in combination with cylindrical sleeve 52, provides a liquid dam for isolating the output shaft of the electric motor 35 from the liquid and other debris in the collection chamber 40.

The cleanliness of the separation chamber 22 is further facilitated by the construction of liquid separator housing 60. The separator housing 60 encompasses and helps define the separator chamber 22. The housing 60 contains a large, substantially cylindrical, cap bore 62 and an annular, substantially flat reference surface 63 surrounding the cap bore 62 on the exterior surface of the housing 60. The housing 60 further includes a substantially cylindrical cap 65 which carries and defines the upper surface 30 of the separation chamber 22. The cap 65 is provided with an annular shoulder 66 which cooperates with the flat reference surface 63 on the exterior of the housing 60 to accurately position the upper surface 30 of the separation chamber 22 relative to the lower surface 31. This is an important feature since it is critical to the proper operation of the liquid separator to maintain the parallelism of upper and lower separator walls 30 and 31 and to maintain the clearance 32 therebetween within a specified range. The cap 65 is provided with an O-ring type seal 69 which is compressed between the cap bore 62 and the cap 65 to mount the cap 65 within the bore 62 in a manual interference type fit. This facilitates the manual removal of the cap 65 for replacement or cleaning and provides access to the separation chamber 22 and the disk 50 for replacement and/or cleaning of the disk. Preferably, the sample gas inlet 20, the sample gas outlet 21 and the inlet and outlet manifolds 25 and 26 are disposed within the cap 65. By molding or otherwise suitably forming the manifolds 25 and 26 within the cap 65, the off-axis distance D separating the points at which the inlet and outlet manifolds communicate with separation chamber 22 can be accurately controlled. This is another important factor since the separation distance D between the inlet and outlet to separation chamber 22 must be controlled within a specified range, 0.10 to 0.30 inches, to insure the proper operation of the separator.

The housing 60 also defines the collection chamber 40 which surrounds the separation chamber 22. The housing further comprises a cylindrical sump bore 70 which is below and in fluid communication with the collection chamber 40. The sump bore 70 receives a substantially cylindrical and translucent sump receptacle or vial 71 which is mounted within the cylindrical sump bore 70 with a manual interference-type fit. An O-ring type seal 72 is compressed between the cylindrical exterior of the sump receptacle 71 and the sump bore 70 to seal the collection chamber 40 and help fix the sump receptacle within the sump bore 70. The sump receptacle 71 defines the lowest portion of the collection chamber 40 and in effect, creates a sight glass which the operator can use to monitor the amount of liquid and other debris being pumped through the liquid separator. The sump exhaust line 46 terminates within the generally cylindrical sump receptacle 71 to apply a negative pressure to the collection chamber 40.

The housing 60 further includes a cylindrical motor bore 80 for receiving the electric motor 35. The cylindrical motor bore 80 is centered on the central axis 36 of separation chamber 22 for accurately aligning the centrally located output shaft of the motor 35 on the central axis 36. Once the cylindrical motor 35 is mounted within the motor bore 80, it is sealed therein with a suitable potting material at 81.

Preferably, the cap 65 and the disk 50 are formed from a hydrophobic, acetal homopolymer material. the suitable material is commercially available and identified by the trademark Delrin. The housing 60 is preferably formed of aluminum which is surface anodized.

As previously indicated, the parallelism of the upper and lower walls 30 and 31 of the separation chamber 22 and the clearance 32 established therebetween is critical to the proper operation of the liquid separator 10. For example, it has been found that if the clearance D is too large then a substantial amount of mixing of the sample gas occurs within the separation chamber 22 substantially decreasing the response time of the separator. Thus, it is critical to maintain a separation distance or clearance 32 which provides for laminar flow through the separation chamber 22 yet which is large enough to provide sufficient sample gas flow through the separation chamber 22 and into the gas outlet 21. The smoothness of the walls 30 and 31 is also critical to the operation of the separator. Both of the walls are very smooth, and they are prepared by polishing with 700 grade wet and dry sandpaper. A common polished finish is approximately 8 rms roughness in microinches.

For example, in a liquid separator designed specifically for use with a nondispersive infrared gas analyzer used in the art of capnography, a separation chamber 22 was formed from a disk 50 having a diameter of approximately 0.9 inches. The disk-shaped member 50 was rotated at approximately 8000 rpm by a DC electric motor 35. The clearance 32 between the upper and lower surfaces 30 and 31 of the separation chamber 22 was maintained within a range between 0.010 and 0.020 inches. The gas outlet manifold 26 received sample gas from a point within the separation chamber 22 coincident with central axis 36. The gas inlet manifold 25 supplied sample gas to the separation chamber 22 at a point disposed approximately 0.2 inches off axis. This separator was found to provide a response time of 100–150 milliseconds, that is to say, within this response time, the separator 10 passed a representative sample of sample gas from inlet 20 to analyzer 18 while substantially separating water, condensate, sputum, mucuous, blood and other liquids or debris entrained in the sample gas flow. These dimensional relationships and specifications result in a substantially uniform migration of the lighter elements in the sample gas from the exterior of the spinning disk inwardly towards the outlet manifold 26 where the vacuum applied by pump 17 draws the cleansed sample through the analyzer 18. This is all accomplished in a substantially laminar fashion while the heavier components and particularly, the liquids entrained in the sample gas flow are quickly accelerated outwardly through contact with the spinning disk 50 and centrifugal acceleration imparted thereto. Any gaseous components are then drawn away by sump exhaust 46 while liquids are collected within the sump receptacle 71.

Another important feature of the water separator 10 of the present invention relates to the fact that the device is fail-safe when the input line 15 is substantially blocked or filled with liquid. This is an important consideration since any of the liquids mentioned herein can completely contaminate the sample chamber of the gas analyzer 18 requiring replacement of the sample chamber and perhaps recalibration of the analyzer 18. The dimensions and specifications set forth above are important since they establish the pressures within the separation chamber 22 which result in the desirable flow and separation characteristics outlined above. During the normal operation of the device, approximately twenty percent (20%) of the sample gas flow is stripped off along with liquid and other debris into the collection chamber 40. Approximately eighty percent (80%) of the sample gas flow is then available to pass through the separation chamber 22 to the analyzer 18. This fairly substantial amount of sample gas flow which is passed directly to the analyzer 18 is, to a large degree, responsible for the remarkable response time of the liquid separator of the present invention. However, with the dimensions and other specifications related above, in the case where the inlet line 15 becomes completely blocked or immersed in liquid such as when the patient 12 inadvertently spits a large amount of saliva or mucous into the tube 13, the gas analyzer of the present invention immediately turns into a liquid pump which is capable of pumping 10 to 20 cc's of liquid per minute into the collection chamber 40. During this pumping action, no sample gas flow is permitted through the separation chamber 22 and out to the analyzer 18. In fact, a significant back flow is observed in the line 41 extending to the analyzer 18 which substantially isolates the sample chamber within the analyzer 18 from the debris and other contaminants which were introduced to the sample gas line 15.

The above description is exemplary and should be considered that of the preferred embodiment only. Modifications to the present invention will occur to those who make and use the invention. It is desired to encompass within the present invention all such modifications that come within the scope of the appended claims.

The embodiments of the invention in which an exclusive property or privilege is claimed are defined as follows:

1. A liquid separator having a small gas flow rate for a gas analyzer comprising:
   a housing;
   a sample gas inlet disposed in said housing;
   a sample gas outlet disposed in said housing;
   a separation chamber disposed within said housing, said separation chamber being in fluid communication with said gas inlet and said gas outlet, said separation chamber having a smooth, planar first wall disposed in said housing and a smooth planar second wall disposed on a rotatable member journaled in said housing, said first and second walls being substantially parallel and having a small uniform clearance therebetween;
   a motor means disposed in said housing and connected to said rotatable member for imparting a rotational velocity to said second wall about a central axis normal to said planar first and second walls;
   said gas outlet being disposed on said central axis is said first wall;
   said gas inlet being positioned in said first wall with an offset from said central axis
   a pump means for establishing a vacuum, said pump means being in flow communication with said sample gas outlet for drawing sample gas through said separation chamber;
   a collection chamber disposed on said housing surrounding said separation chamber, said collection chamber being positioned to receive liquids and other debris separated by contact with said second wall and centrifugal acceleration imparted thereto by rotation of said second wall;
   said pump means being in flow communication with said collection chamber for applying a vacuum thereto;
   a removable liquid sump disposed below and in fluid communication with said collection chamber.

2. The liquid separator of claim 1 wherein said rotatable member comprises a substantially disk-shaped member, and said motor means comprises an electric motor having an output shaft, said disk-shaped member being mounted for rotation on said output shaft of said electric motor, said output shaft of said electric motor being coincident with said central axis.

3. The liquid separator of claim 2 wherein said disk-shaped member is provided with a central bore which receives said output shaft of said electric motor with a manually demountable interference fit and facilitating replacement and cleaning of said disk-shaped member.

4. The liquid separator of claim 2 wherein said disk-shaped member is provided with a concave, conical surface on the underside thereof for creating a liquid dam which isolates said output shaft from liquid and debris in said collection chamber.

5. The liquid separator of claim 2 wherein said separation chamber and said collection chamber are both disposed within said housing, said housing having a cylindrical motor bore, said electric motor being received in said cylindrical motor bore, said cylindrical motor bore being centered on said central axis and sdid electric motor being sealed therein with a potting material.

6. The liquid separator of claim 2 wherein said disk-shaped member is formed from an acetal homopolymer material.

7. The liquid separator of claim 2 wherein said disk-shaped member has a diameter of approximately 0.9 inches, said disk-shaped member is rotated at approximately 8,000 RPM, said clearance between said upper and lower surface is within a range of 0.010 and 0.020 inches, said gas inlet has an offset of approximately 0.2 inches, and said separator is particularly adapted for separating blood, mucous, condensate and other materials encountered in a sample of human breath gases.

8. The liquid separator of claim 1 wherein said housing is provided with a large, substantially cylindrical cap bore and an annular, substantially flat reference surface surrounding said cap bore; said housing having a substantially cylindrical cap defining said first wall of said separation chamber and said cap having an annular shoulder which cooperates with said flat reference surface to accurately position said first wall of said separation chamber relative to said second wall.

9. The liquid separator of claim 8 wherein said cap is provided with an O-ring type seal which is compressed between said cap and said cylindrical cap bore, and said cap is received in said cap bore with a manual interference-type fit to facilitate removal and cleaning of said cap.

10. The liquid separator of claim 8 wherein said gas inlet and said gas outlet are disposed in said cap.

11. The liquid separator of claim 8 wherein said housing is formed from anodized aluminum.

12. The liquid separator of claim 8 wherein said cap is formed from an acetal homopolymer material.

13. The liquid separator of claim 1 wherein said separation chamber and said collection chamber are both disposed within said housing, said housing having a cylindrical sump bore below and in fluid communication with said collection chamber, said removable liquid sump comprising a substantially cylindrical and translucent sump receptacle which is mounted with a manual interference-type fit with an O-ring type seal disposed between said sump bore and said receptacle to facilitate removal and cleaning of said sump receptacle.

14. A liquid separator having a small gas flow rate for a breath gas $CO_2$ gas analyzer used in the art of capnography comprising:
   a housing;
   a sample gas inlet disposed in said housing;
   a sample gas outlet disposed in said housing;
   a separation chamber disposed within said housing, said separation chamber being in fluid communication with said gas inlet and said gas outlet, said separation chamber having a smooth, planar first wall which includes said gas inlet and sawd gas outlet, and a smooth, planar second wall disposed on a member mounted for rotatable rotation within said housing, said first and second walls being substantially parallel and having a small uniform clearance therebetween in a range of 0.010 and 0.020 inches;
   a motor means disposed in said housing for driving said rotatable member and imparting a rotational velocity to said second wall about a central axis normal to said planar first and second walls, said motor means operating in a range of 5,000 to 10,000 RPM;

said gas outlet being disposed in said first wall on said central axis;

said gas inlet being positioned in said first wall and being provided with an offset relative to said central axis in a range of 0.10 to 0.30 inches;

a collection chamber disposed within said housing, said collection chamber at least partially surrounding said separation chamber, said collection chamber being positioned to receive liquids and other debris separated by contact with said second wall and centrifugal acceleration imparted thereto by rotation of said second wall;

a pump means for establishing a vacuum, said pump means being in fluid communication with said sample gas outlet for drawing sample gas through said separation chamber, and said collection chamber to facilitate the exit of liquid and other debris from said separation chamber; and said pump means being in flow communication with said collection chamber for applying a vacuum thereto;

a removable liquid sump disposed below and in fluid communication with said collection chamber.

15. A liquid separator having a small gas flow rate for a gas analyzer comprising:

a housing;

a sample gas inlet disposed in said housing;

a sample gas outlet disposed in said housing;

a separation chamber disposed within said housing, said separation chamber being in fluid communication with said gas inlet and said gas outlet, said separation chamber having a smooth, planar first wall disposed in said housing and a smooth planar second wall disposed on a rotatable member journaled in said housing, said first and second walls being substantially parallel and having a small uniform clearance therebetween;

a motor means disposed in said housing and connected to said rotatable member for imparting a rotational velocity to said second wall bout a central axis normal to said planar first and second walls;

said gas outlet being disposed on said central axis in said first wall;

said gas inlet being positioned in said first wall with an offset from said central axis;

a pump means for establishing a vacuum, said pump means being in flow communication with said sample gas outlet for drawing sample gas through said separation chamber;

a collection chamber disposed on said housing surrounding said separation chamber, said collection chamber being positioned to receive liquids and other debris separated by contact with said second wall and centrifugal acceleration imparted thereto by rotation of said second wall;

said housing being provided with a large, substantially cylindrical cap bore and an annular, substantially flat reference surface surrounding said cap bore; said housing having a substantially cylindrical cap defining said first wall of said separation chamber and said cap having an annular shoulder which cooperates with said flat reference surface to accurately position said first wall of said separation chamber relative to said second wall.

* * * * *